US006623755B2

(12) United States Patent
Chen et al.

(10) Patent No.: US 6,623,755 B2
(45) Date of Patent: Sep. 23, 2003

(54) PHARMACEUTICAL TABLETS

(75) Inventors: Tzyy-Show H. Chen, Princeton Junction, NJ (US); Thomas G. Nyairo, Norristown, PA (US); Ashok V. Katdare, Norristown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/099,672

(22) Filed: Mar. 15, 2002

(65) Prior Publication Data

US 2002/0187186 A1 Dec. 12, 2002

Related U.S. Application Data

(63) Continuation of application No. 09/881,285, filed on Jun. 14, 2001, which is a continuation of application No. 09/605,513, filed on Jun. 28, 2000, now abandoned.
(60) Provisional application No. 60/141,987, filed on Jul. 1, 1999.

(51) Int. Cl.$^7$ .............................. A61K 9/20; A61K 9/42; A61K 9/16; A61K 9/28; A61K 9/22
(52) U.S. Cl. ........................ 424/464; 465/476; 465/480; 465/494; 465/498; 465/475; 465/474; 465/468
(58) Field of Search ................................. 424/464, 465, 424/476, 460, 494, 498, 475, 474, 468

(56) References Cited

U.S. PATENT DOCUMENTS

| | | | |
|---|---|---|---|
| 4,054,598 A | 10/1977 | Blum et al. | |
| 4,267,108 A | 5/1981 | Blum et al. | |
| 4,621,077 A | 11/1986 | Rosini et al. | |
| 4,942,157 A | 7/1990 | Gall et al. | |
| 4,948,622 A | 8/1990 | Kokubo et al. | |
| 5,041,428 A | 8/1991 | Isomura et al. | |
| 5,047,246 A | 9/1991 | Gallian et al. | |
| 5,070,108 A | 12/1991 | Margolis | |
| 5,158,944 A | 10/1992 | Makino et al. | |
| 5,358,941 A | * 10/1994 | Bechard et al. | ............. 514/102 |
| 5,681,590 A | 10/1997 | Bechard et al. | |
| 5,882,656 A | 3/1999 | Bechard et al. | |
| 5,958,908 A | 9/1999 | Dohi et al. | |

FOREIGN PATENT DOCUMENTS

| | | |
|---|---|---|
| GB | 1036368 | 7/1966 |
| WO | WO 97/39755 | 10/1997 |
| WO | WO 98/18610 | 5/1998 |
| WO | WO 98/56360 | 12/1998 |
| WO | WO 00/00179 | 1/2000 |

OTHER PUBLICATIONS

Physician's Desk Reference, 44th ed., (1990), p. 1534, "Didronel (etidronate disodium)".
Lachman et al., The Theory and Practice of Industrial Pharmacy, 3rd ed., (1986), p. 326.
Remington's Pharmaceutical Science, 15th ed., Mack Pub. Co., Easton, PA, Chap 89, pp. 1586–1588.

* cited by examiner

Primary Examiner—Thurman K. Page
Assistant Examiner—Blessing Fubara
(74) Attorney, Agent, or Firm—James M. Hunter, Jr.; Mark R. Daniel

(57) ABSTRACT

The present invention relates to novel pharmaceutical tablets useful for administering pharmaceutical active ingredients, such as bisphosphonates. These tablets have improved surface properties which can aid esophageal transit, thereby reducing the potential for adverse gesture intestinal effects. The present invention also relates to processes for making said novel pharmaceutical tablets.

18 Claims, No Drawings

PHARMACEUTICAL TABLETS

CROSS-REFERENCE TO RELATED APPLICATIONS

This is a continuation of application Ser. No. 09/881,285, filed Jun. 14, 2001, which is a continuation of application Ser. No. 09/605,513, filed Jun. 28, 2001 now abandoned, which in turn claims priority to U.S. Provisional Application Serial No. 60/141,987, filed Jul. 1, 1999, now abandoned.

FIELD OF THE INVENTION

The present invention relates to novel pharmaceutical tablets. These tablets have improved surface properties which can aid esophageal transit, thereby reducing the potential for adverse gastrointestinal effects. These compositions are useful for administering pharmaceutical active ingredients, such as bisphosphonates.

BACKGROUND OF THE INVENTION

The pharmaceutical industry employs various methods for compounding pharmaceutical agents into oral tablet formulations. Standard methods for tablet formulation of bisphosphonic acids, however, suffer serious difficulties.

In particular, bisphosphonic acids which bear a basic nitrogen-containing functionality may interact with the lactose of standard formulations resulting in discoloration, instability and potency loss. This degradation of the active ingredient is particularly pronounced in the presence of water and/or elevated temperatures. It is speculated that this incompatibility is specifically due to the Maillard (or "browning") reaction in which the free amino group of the bisphosphonic acid reacts with the "glycosidic" hydroxyl group of a sugar (such as lactose) ultimately resulting in the formation of brown pigmented degradates. Although this problem may be avoided by the elimination if lactose, the use of lactose as an inert diluent is generally desirable.

The present invention solves this problem by providing a tablet formulation and process therefore that avoids such interaction between the bisphosphonic acid and the lactose in the formulation. In addition the present invention provides a processing advantage since it requires only blending of the ingredients without granulation or addition of water prior to compression.

In addition to compounding problems, bisphosphonates are poorly absorbed from the gastrointestinal tract. See B. J. Gertz et al., *Clinical Pharmacology of Alendronate Sodium, Osteoporosis Int.*, Suppl. 3: S13–16 (1993) and B. J. Gertz et al., *Studies of the oral bioavailability of alendronate, Clinical Pharmacology & Therapeutics*, vol. 58, number 3, pp. 288–298 (Sep. 1995), which are incorporated by reference herein in their entirety. Intravenous administration has been used to overcome this bioavailability problem. However, intravenous administration is costly and inconvenient, especially when the patient must be given an intravenous infusion lasting several hours on repeated occasions. If oral administration of the bisphosphonate is desired, relatively high doses must be administered to compensate for the low bioavailability from the gastrointestinal tract. To offset this low bioavailability, it is generally recommended that the patient take the bisphosphonate on an empty stomach and fast for at least 30 minutes afterwards. However, many patients find the need for such fasting on a daily basis to be inconvenient.

Moreover, oral administration of bisphosphonates has been associated with adverse gastrointestinal effects, especially those relating to the esophagus. See H. Fleisch, *Bisphosphonates in Bone Disease, from the laboratory to the patient*, third edition, 1997. Such oral administration of bisphosphonates sometimes results in patient complaints shortly after dosing; said complaints are usually characterized by the patients as heartburn, esophageal burning, pain and/or difficulty upon swallowing, and/or pain existing behind and/or mid-sternum. It is believed that these complaints originate from esophagitis or esophageal irritation caused by the erosion, ulceration, or other like irritation or the epithelial and mucosal tissues, resulting in the topical irritation thereof. If the dosage form adheres in the esophagus, the active ingredient slowly dissolves and creates a high drug concentration on the mucosal surface of the esophagus.

These unfavorable effects are exacerbated by the presence of refluxed gastric acid. For example, the bisphosphonate, pamidronate has been associated with esophageal ulcers. See E. G. Lufkin et al., *Pamidronate: An Unrecognized Problem in Gastrointestinal Tolerability, Osteoporosis International*, 4: 320–322 (1994), which is incorporated by reference herein in its entirety. Although not as common, the use of alendronate has been associated with esophagitis and/or esophageal ulcers. See P. C. De Groen, et al., *Esophagitis Associated With The Use Of Alendronate, New England Journal of Medicine*, vol. 335, no. 124, pp. 1016–1021 (1996), D. O. Castell, *Pill Esophagitis—The Case of Alendronate, New England Journal of Medicine*, vol. 335, no. 124, pp. 1058–1059 (1996), and U. A. Liberman et al., *Esophagitis and Alendronate, New England Journal of Medicine*, vol. 335, no. 124, pp. 1069–1070 (1996), which are incorporated by reference herein in their entirety. The degree of adverse gastrointestinal effects of bisphosphonates has been shown to increase with increasing dose. See C. H. Chestnut et al., *Alendronate Treatment of the Postmenopausal Osteoporotic Woman: Effect of Multiple Dosages on Bone Mass and Bone Remodeling, The American Journal of Medicine*, vol. 99, pp. 144–152, (August 1995), which is incorporated by reference herein in its entirety. Also, these adverse esophageal effects appear to be more prevalent in patients who do not take the bisphosphonate with an adequate amount of liquid or who lie down shortly after dosing, thereby increasing the chance for esophageal reflux.

What is needed in the art is an oral bisphosphonate dosage form that minimizes the adverse side effects enumerated above. Such a dosage form should prevent and/or lessen the degree of patient discomfort while maximizing the treatment by maintaining the bioavailability of the bisphosphonate.

However, dosage forms of bisphosphonates that are presently being used are problematic. For example, rough, unpolished tablets are useful in order to maintain the bioavailability of the active ingredient. Despite this benefit, the rough texture provides for poor esophageal transit which causes the bisphosphonate to be released too early in the upper gastrointestinal tract, causing the patient discomfort.

To combat the premature release of active ingredient in the upper gastrointestinal tract, dosage forms have been developed to delay the release of the active ingredients after passage through the upper gastrointestinal tract and in some cases through the stomach, i.e., enteric coated tablets. However, enteric and completely coated tablets have disadvantages because in certain instances its undesirable or unnecessary for a medicament to be in a delayed release dosage form. Additionally, enteric and completely coated tablets reduce the bioavailability of the active ingredient.

What is desired in the art are dosage forms that facilitate rapid esophageal transit, minimize or avoid the release of an active ingredient in the upper gastrointestinal tract, deliver the active ingredient to the stomach, and maintain the bioavailability of the active ingredient.

The present invention solves this problem by providing a tablet formulation and process therefor that both facilitates esophageal transit and maintains the bioavailability of the active ingredient. The discontinuous wax polish of the present invention has surprisingly been found to be useful for administering active agents such as bisphosphonates. These tablets with a discontinuous wax polish have the advantage of providing rapid transit through the esophagus to minimize the occurrence of adverse effects. The discontinuous wax coating or polishing also has the advantage over enteric coated tablets of not interfering with the bioavailability of the active ingredient. Thus, the current invention provides a dosage form that eases and/or eliminates patient discomfort after dosing while maintaining the bioavailability of the active ingredient.

It is an object of the invention to provide a pharmaceutical composition, preferably a tablet comprising: an active ingredient, said active ingredient being a bisphosphonic acid or a pharmaceutically acceptable salt or ester thereof; excipients, said excipients comprising a diluent, a binder, a disintegrant and a lubricant; and a discontinuous wax polish.

It is another object of the present invention to provide a process for the preparation of a tablet as described above.

These and other objects will become apparent to those of ordinary skill from the teachings provided herein.

The application refers to a number of publications, patents and patent applications the contents of which are hereby incorporated by reference in their entirety.

SUMMARY OF THE INVENTION

The present invention relates to novel pharmaceutical compositions, particularly tablets. These compositions have improved surface properties which can aid esophageal transit, thereby reducing the potential for adverse gastrointestinal effects. These compositions are useful for administering pharmaceutical active ingredients, such as bisphosphonates.

In one embodiment, the present invention relates to a pharmaceutical tablet, comprising:

(a) from about 0.5 to 40% by weight of an active ingredient selected from the group consisting of a bisphosphonic acid or a pharmaceutically acceptable salt or ester thereof; and (b) from about 60 to 99.5% by weight of excipients, said excipients comprising a diluent selected from the group consisting of anhydrous lactose or hydrous fast flow lactose, or mixtures thereof, a binder, a disintegrant, a lubricant; and a wax.

In another embodiment, the present invention relates to a process for the preparation of a pharmaceutical tablet comprising;

(a) forming a mixture by mixing an active ingredient selected from the group consisting of a bisphosphonic acid or a pharmaceutically acceptable salt or ester thereof, with a diluent, selected from the group consisting of anhydrous lactose or hydrous fast flow lactose, or mixtures thereof, a dry binder, a disintegrant, and optionally one or more additional ingredients selected from the groups consisting of: compression aids, flavors, flavor enhancers, sweeteners and preservatives;

(b) lubricating the mixture with a lubricant;

(c) compressing the resultant lubricated mixture into a desired tablet form; and (d) coating the desired tablet with a wax to form a discontinuous wax polish.

All percentages and ratios used herein, unless otherwise indicated, are by weight. The invention hereof can comprise, consist of, or consist essentially of the essential as well as optional ingredients, components, and methods described herein.

DETAILED DESCRIPTION OF THE INVENTION

The present invention relates to novel pharmaceutical compositions, particularly tablets, that are useful for administering pharmaceutical active ingredients, such as bisphosphonates. The compositions of the present invention are coated with a discontinuous wax polish that enables the compositions to have improved surface properties such as rapid esophageal transit of the composition, which reduces the potential for adverse gastrointestinal effects. The improved surface properties due to the discontinuous wax polish also enable the compositions to maintain the bioavailability of the active ingredient, thereby preserving the active ingredient's potency.

The present invention is characterized by pharmaceutical compositions comprising from about 0.5 to 40% by weight of an active ingredient, said active ingredient being a bisphosphonic acid or a pharmaceutically acceptable salt or ester thereof; from about 60 to 99.5% by weight of excipients, said excipients comprising a diluent selected from the group consisting of anhydrous lactose or hydrous fast flow lactose, a binder, a disintegrant, a lubricant; and a discontinuous wax polish.

Preferably, the bisphosphonic acid or pharmaceutically acceptable salt or ester thereof is a nitrogen containing bisphosphonate or pharmaceutically acceptable salt thereof.

More preferably, the nitrogen containing bisphosphonate or pharmaceutically acceptable salt thereof is selected from the group consisting of:

4-amino-1-hydroxybutylidene-1,1-bisphosphonic acid;

N-methyl-4-amino-1-hydroxybutylidene-1,1-bisphosphonic acid;

4-(N,N-dimethylamino)-1-hydroxypropylidene-1,1-bisphosphonic acid;

3-amino-1-hydroxypropylidene-1,1-bisphosphonic acid;

3-(N,N-dimethylamino)-1-hydroxypropylidene-1,1-bisphosphonic acid;

1-hydroxy-3-(N-methyl-N-pentylamino)propylidene-1,1-bisphosphonic acid;

1-hydroxy-2-[3-pyridyl]ethylidene-1,1-bisphosphonic acid; and 4-(hydroxymethylene-1,1-bisphosphonic acid)piperidene;

or a pharmaceutically acceptable salt thereof.

More preferably, the nitrogen containing bisphosphonic acid or pharmaceutically acceptable salt thereof is 4-amino-1-hydroxybutylidene-1,1-bisphosphonic acid or a pharmaceutically acceptable salt thereof.

Most preferably, the nitrogen containing bisphosphonic acid or pharmaceutically acceptable salt thereof is 4-amino-1-hydroxybutylidene-1,1-bisphosphonic acid monosodium salt trihydrate.

The present invention is also characterized by to pharmaceutical compositions comprising from about 0.5 to 40% by weight of an active ingredient, said active ingredient being a bisphosphonic acid or a pharmaceutically acceptable salt thereof; from about 60 to 99.5% by weight of excipients, said excipients comprising a diluent selected from the group consisting of anhydrous lactose or hydrous fast flow lactose, a binder, a disintegrant, a lubricant; and a discontinuous wax polish; wherein said pharmaceutical composition is in a desired tablet form.

Preferably, the bisphosphonic acid or pharmaceutically acceptable salt thereof is a nitrogen containing bisphosphonate or pharmaceutically acceptable salt thereof.

More preferably, the nitrogen containing bisphosphonate or pharmaceutically acceptable salt thereof is selected from the group consisting of:
4-amino-1-hydroxybutylidene-1,1-bisphosphonic acid;
N-methyl-4-amino-1-hydroxybutylidene-1,1-bisphosphonic acid;
4-(N,N-dimethylamino)-1-hydroxypropylidene-1,1-bisphosphonic acid;
3-amino-1-hydroxypropylidene-1,1-bisphosphonic acid;
3-(N,N-dimethylamino)-1-hydroxypropylidene-1,1-bisphosphonic acid;
1-hydroxy-3-(N-methyl-N-pentylamino)propylidene-1,1-bisphosphonic acid;
1-hydroxy-2-[3-pyridyl]ethylidene-1,1-bisphosphonic acid; and
4-(hydroxymethylene-1,1-bisphosphonic acid)piperidene;
or a pharmaceutically acceptable salt thereof.

More preferably, the nitrogen containing bisphosphonic acid or pharmaceutically acceptable salt thereof is 4-amino-1-hydroxybutylidene-1,1-bisphosphonic acid or a pharmaceutically acceptable salt thereof.

Most preferably, the nitrogen containing bisphosphonic acid or pharmaceutically acceptable salt thereof is 4-amino-1-hydroxybutylidene-1,1-bisphosphonic acid monosodium salt trihydrate.

The present invention also relates to processes for the production of pharmaceutical compositions and tablets. The processes include coating the compositions or tablets with a discontinuous wax polish which provides advantages over completely coated compositions and tablets. Because the compositions or tablets are discontinuously coated, the bioavailability of the active ingredient is preserved.

The present invention is also characterized by processes for the preparation of a tablet containing an active ingredient, said active ingredient being a bisphosphonic acid or a pharmaceutically acceptable salt thereof; which process comprises:

forming a mixture by mixing the active ingredient with:
a diluent, selected from the group consisting of anhydrous lactose and hydrous fast flow lactose and mixtures thereof,
a dry binder,
a disintegrant,
and optionally one or more additional ingredients selected from the groups consisting of: compression aids, flavors, flavor enhancers, sweeteners and preservatives;
lubricating the mixture with a lubricant;
compressing the resultant lubricated mixture into a desired tablet form; and
coating the desired tablet form with a discontinuous wax polish.

Preferably, the bisphosphonic acid or pharmaceutically acceptable salt thereof is a nitrogen containing bisphosphonate or pharmaceutically acceptable salt thereof.

More preferably, the nitrogen containing bisphosphonate or pharmaceutically acceptable salt thereof is selected from the group consisting of:
4-amino-1-hydroxybutylidene-1,1-bisphosphonic acid;
N-methyl-4-amino-1-hydroxybutylidene-1,1-bisphosphonic acid;
4-(N,N-dimethylamino)-1-hydroxypropylidene-1,1-bisphosphonic acid;
3-amino-1-hydroxypropylidene-1,1-bisphosphonic acid;
3-(N,N-dimethylamino)-1-hydroxypropylidene-1,1-bisphosphonic acid;
1-hydroxy-3-(N-methyl-N-pentylamino)propylidene-1,1-bisphosphonic acid;
1-hydroxy-2-[3-pyridyl]ethylidene-1,1-bisphosphonic acid; and
4-(hydroxymethylene-1,1-bisphosphonic acid)piperidene;
or a pharmaceutically acceptable salt thereof.

More preferably, the nitrogen containing bisphosphonic acid or pharmaceutically acceptable salt thereof is 4-amino-1-hydroxybutylidene-1,1-bisphosphonic acid or a pharmaceutically acceptable salt thereof.

Most preferably, the nitrogen containing bisphosphonic acid or pharmaceutically acceptable salt thereof is 4-amino-1-hydroxybutylidene-1,1-bisphosphonic acid monosodium salt trihydrate.

Preferably, the dry binder is microcrystalline cellulose.

Preferably, the disintegrant is selected from the group consisting of modified starch, modified cellulose polymer, and croscarmellose sodium, or a combination thereof.

More preferably, the disintegrant is croscarmellose sodium.

Preferably, the lubricant is magnesium stearate.

Preferably, no additional water is added to the mixture prior to compressing.

Preferably, the processes are carried out at ambient temperature.

More preferably, no additional water is added to the mixture prior to compressing and said process is carried out at ambient temperature.

The word wax, which had originally referred to relatively high melting animal or vegetable derived lipids, is applied to a large variety of chemically different lipids in modem parlance. Included as waxes are animal waxes, plant waxes, mineral waxes and petroleum waxes. See International Cosmetic Ingredient Dictionary and Handbook, Seventh Edition, vol. 1, p. 1604–05 (1997), which is hereby incorporated by reference in its entirety.

Preferably, the discontinuous wax polish is selected from the group consisting of: apple peel wax, avocado wax, bayberry wax, beeswax, candelilla wax, carnauba wax, ceresin, cetyl esters, hydrogenated jojoba oil, hydrogenated jojoba wax, hydrogenated microcrystalline wax, hydrogenated rice bran wax, hydrolyzed beeswax, jojoba butter, jojoba esters, jojoba wax, lanolin wax, microcrystalline wax, mink wax, montan acid wax, mantan wax, orange peel wax, ouricury wax, oxidized beeswax, oxidized microcrystalline wax, ozokerite, palm kernel wax, paraffin, PEG-6 Beeswax, PEG-8 Beeswax, PEG-12 Beeswax, PEG-20 Beeswax, PEG-12 Carnauba, potassium oxidized microcrystalline wax, rice wax, shellac wax, spent grain wax, sulfurized jojoba oil, synthetic beeswax, synthetic candelilla wax, synthetic carnauba, synthetic Japan wax, synthetic jojoba oil, synthetic wax, and mixtures thereof.

More preferably, the discontinuous wax polish is carnauba wax.

Carnauba wax, which is also known as brazil wax or caranda wax, is the hardest and highest melting of the waxes commonly used in pharmaceutical formulations. It can be used as an aqueous emulsion or a powder to polish tablets. See Handbook of Pharmaceutical Excipients, Second Edition, p. 552 (1994), which is hereby incorporated by reference in its entirety.

Beeswax can be obtained naturally (yellow beeswax) or chemically bleached (white beeswax). Beeswax consists of 70–75% of a mixture of various esters of straight chain monohydric alcohols with even number carbon chains, the chief ester being myricyl palmitate. Beeswax is primarily used as a-stiffening agent, an emulsifier, or a polishing agent for tablets. See Handbook of Pharmaceutical Excipients, Second Edition, p. 558–60 (1994).

Microcrystalline wax, which is also known as amorphous wax and petroleum ceresin, is used to modify the crystal structure of other waxes present in a mixture so that changes in crystal structure, which are usually exhibited over a period of time, do not occur. Microcrystalline wax also prevents blends of waxes from sweating or bleeding. See Handbook of Pharmaceutical Excipients, Second Edition, p. 554 (1994).

Paraffin, which is also known as hard wax, paraffinium solidum, and paraffinium durum, is a purified mixture of solid saturated hydrocarbons having the general formula $C_nH_{2n}+2$. It is generally obtained from petroleum or shale oil. See Handbook of Pharmaceutical Excipients, Second Edition, p. 327 (1994).

Cetyl esters wax, which is also known as spermaceti wax replacement and synthetic spermaceti, is a mixture consisting primarily of esters of saturated fatty alcohols and saturated fatty acids. See Handbook of Pharmaceutical Excipients, Second Edition, p. 104 (1994).

Shellac wax, which is also known as lacca and lac, is a naturally occurring material that is used in pharmaceutical formulations for the coating of tablets. Shellac wax is usually applied as a 35% w/v alcoholic solution, but is also applied as a 40% w/v alcoholic solution when sealing tablets to protect them from moisture before being film or sugar coated. Shellac is insoluble in acidic conditions but soluble at higher pHs. See Handbook of Pharmaceutical Excipients, Second Edition, p. 422–23 (1994).

The pharmaceutical compositions and tablets of the present invention are generally administered to mammals in need of bisphosphonate therapy. Preferably the mammals are human patients, particularly human patients in need of inhibiting bone resorption, such as patients in need of treating or preventing abnormal bone resorption.

The pharmaceutical compositions and tablets of the present invention are especially useful in administering bisphosphonate therapy to human patients that have been identified as suffering from or are susceptible to upper gastrointestinal disorders, e.g. GERD, esophagitis, dyspepsia, ulcers, etc. In such patients conventional bisphosphonate therapy could potentially exacerbate or induce such upper gastrointestinal disorders.

The term "discontinuous wax polish," as used herein, means a wax polish that is not continuously applied to the surface area of a pharmaceutical tablet. Accordingly, the wax polish is applied to the pharmaceutical tablet such that about 1 to 99% of the surface area of the tablet is coated with wax polish.

The term "pharmaceutical tablet," as used herein, means a solid dosage form that contains a excipients and a pharmaceutically effective amount of bisphosphonate compound that will elicit the desired therapeutic effect or response when administered in accordance with the desired treatment regimen.

The term "surface area," as used herein, means the exterior area of a pharmaceutical tablet.

The term "pharmaceutically effective amount", as used herein, means that amount of the bisphosphonate compound, that will elicit the desired therapeutic effect or response when administered in accordance with the desired treatment regimen. A preferred pharmaceutically effective amount of the bisphosphonate is a bone resorption inhibiting amount.

The term "minimize the occurrence of or potential for adverse gastrointestinal effects", as used herein, means reducing, preventing, decreasing, or lessening the occurrence of or the potential for incurring unwanted side effects in the gastrointestinal tract, i.e. the esophagus, stomach, intestines, and rectum, particularly the upper gastrointestinal tract, i.e. the esophagus and stomach. Non-limiting adverse gastrointestinal effects include, but are not limited to GERD, esophagitis, dyspepsia, ulcers, esophageal irritation, esophageal perforation, abdominal pain, and constipation.

The term "pharmaceutically acceptable" as used herein means that the salts and derivatives of the bisphosphonates have the same general pharmacological properties as the free acid form from which they are derived and are acceptable from a toxicity viewpoint.

The term "pharmaceutically acceptable salt", as used herein refers to non-toxic salts of the compounds useful in the instant invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Pharmaceutically acceptable salts also specifically include hydrates as well as the anhydrous forms.

Dosage regimens utilizing the compounds of the present invention are selected in accordance with a variety of factors including type, species, age, weight, sex and medical condition of the patient or subject; the severity of the condition to be treated; the route of administration; the renal and hepatic function of the patient or subject; and the particular compound or salt thereof employed. An ordinarily skilled physician, veterinarian or clinician can readily determine and prescribe the effective amount of the drug required to reduce the risk of, counter or arrest the progress of the condition.

Oral dosages of the present invention, when used for the indicated effects, will range between about 0.05 mg per kg of body weight per day (mg/kg/day) to about 1.0 mg/kg/day. For example, as a treatment, alendronate would be administered to mammals in preferred doses of about 2.5 mg to about 50 mg daily, preferably about 5 mg for osteoporosis treatment and about 10 mg for osteoporosis prevention, and about 40 mg Paget's disease. Alternatively, dosages of about 8.75 to about 70 mg once-weekly or twice-weekly. Preferred weekly dosages are about 35 mg, e.g., for osteoporosis prevention and about 70 mg, e.g., for osteoporosis treatment. Preferred twice-weekly dosage are about 17.5 mg, e.g., for osteoporosis prevention and about 35 mg, e.g., for osteoporosis treatment. The dosages may be varied over time, such that a patient may receive a high dose, such as 20 mg/day for a treatment period, such as two years, followed by a lower dose thereafter, such as 5 mg/day thereafter. Alternatively, a low dose (i.e. approximately 5 mg) may also be administered for a longer term with similar beneficial effects. Oral doses of the present invention can be administered in a single daily dose or in a divided dose.

Bisphosphonates

The methods and compositions of the present invention comprise the administration of a bisphosphonate or a pharmaceutically acceptable salt thereof. The bisphosphonates of the present invention correspond to the chemical formula

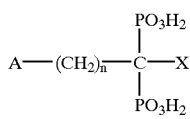

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, non-limiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, non-limiting examples of which include naphthyl, quinolyl, isoquinolyl, adamantyl, and chlorophenylthio.

A non-limiting class of structures useful in the instant invention are those in which A is selected from the group consisting of H, OH, and halogen, and X is selected from the group consisting of C1–C30 alkyl, C1–C30 substituted alkyl, halogen, and C1–C10 alkyl or phenyl substituted thio.

A non-limiting subclass of structures useful in the instant invention are those in which A is selected from the group consisting of H, OH, and Cl, and X is selected from the group consisting of C1–C30 alkyl, C1–C30 substituted alkyl, Cl, and chlorophenylthio.

A non-limiting example of the subclass of structures useful in the instant invention is when A is OH, X is a 3-aminopropyl moiety and n is zero, so that the resulting compound is a 4-amino-1,-hydroxybutylidene-1,1-bisphosphonate, i.e. alendronate.

Pharmaceutically acceptable salts and derivatives of the bisphosphonates are also useful herein. Non-limiting examples of salts include those selected from the group consisting alkali metal, alkaline metal, ammonium, and mono-, DI, tri-, or tetra-C1–C30-alkyl-substituted ammonium. Preferred salts are those selected from the group consisting of sodium, potassium, calcium, magnesium, and ammonium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those or ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and J. Org. Chem 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zolendronate).

A non-limiting class of bisphosphonates useful in the instant invention are selected from the group consisting of alendronate, cimadronate, clodronate, tiludronate, etidronate, ibandronate, risedronate, piridronate, pamidronate, zolendronate, pharmaceutically acceptable salts thereof, and mixtures thereof.

A non-limiting subclass of the above-mentioned class useful in the instant case contains alendronate, pharmaceutically acceptable salts thereof, and mixtures thereof.

A non-limiting example of the subclass is alendronate monosodium trihydrate.

Pharmaceutical Compositions

The compounds of the present invention can be administered in such oral dosage forms as tablets, capsules (each of which includes sustained release or timed release formulations), pills, powders, granules, elixirs, tinctures, suspensions, syrups, pastes, gels, solutions, and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as a treatment for dental resorptive lesions.

Compositions useful in the present invention comprise a pharmaceutically effective amount of a bisphosphonate or a pharmaceutically acceptable salt thereof. The bisphosphonate is typically administered in admixture with suitable pharmaceutical diluents, excipients, or carriers, collectively referred to herein as "carrier materials", suitably selected with respect to oral administration, i.e. tablets, capsules, elixirs, syrups, effervescent compositions, powders, and the like, and consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs and syrups, effervescent compositions, the oral drug components can be combined with any oral, non-toxic, pharmaceutically acceptable inert carrier such as ethanol, glycerol, water and the like. Moreover, when desired or necessary, suitable binders, lubricants, disintegrating agents, buffers, coatings, and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A tablet formulations for alendronate monosodium trihydrate and other bisphosphonates are described in U.S. Pat. No. 5,358,941, to Bechard et al, issued Oct. 25, 1994, and U.S. Pat. No. 5,681,590, to Bechard et al., issued Oct. 28, 1997, which are both incorporated by reference herein in its entirety. Oral liquid alendronate formulations are described in U.S. Pat. No. 5,462,932, to Brenner et al, issued Oct. 31, 1995, which is incorporated by reference herein in its entirety. Intravenous alendronate formulations are described in U.S. Pat. No. 5,780,455, to Brenner et al, issued Jul. 14, 1998, which is incorporated by reference herein in its entirety. The compounds used in the present method can also be coupled with soluble polymers as targetable drug carriers. Such polymers can include polyvinylpyrrolidone, pyran copolymer, polyhydroxylpropyl-methacrylamide, and the like.

The precise dosage of the bisphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a dental resorptive lesion inhibiting effect.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

Pharmaceutical Tablet Compositions

Tablets are prepared using standard mixing and formation techniques as described in U.S. Pat. No. 5,358,941, to Bechard et al., issued Oct. 25, 1994, which is incorporated by reference herein in its entirety. The tablets are polished with a discontinuous film of the desired wax using a coating pan, a coating column, a blender, or equivalent equipment.

For example, tablets containing about 10 mg or 70 mg of alendronate monosodium trihydrate, on an alendronic acid active basis, are prepared using the following relative weights of ingredients.

| Ingredient | 10 mg Tablet Per Tablet | 70 mg Tablet Per Tablet |
| --- | --- | --- |
| Alendronate Monosodium Trihydrate | 13.05 mg | 91.37 mg |
| Anhydrous Lactose, NF | 104 mg | 114 mg |
| Microcrystalline Cellulose, NF | 80 mg | 140 mg |
| Magnesium Stearate, NF | 1 mg | 1.75 mg |
| Croscarmellose Sodium, NF | 2 mg | 3.5 mg |
| Carnauba Wax | 0.2 mg | 0.2 mg |

The resulting tablets are useful for administration in accordance with the methods of the present invention for inhibiting bone resorption.

Similarly, tablets comprising other relative weights of alendronate, on an alendronic acid active basis are prepared: e.g., tablets containing about 5, 8.75, 17.5, 35 and 140 mg per tablet. Also, tablets containing other bisphosphonates at appropriate active levels are similarly prepared: e.g., cimadronate, clodronate, tiludronate, etidronate, ibandronate, risedronate, piridronate, pamidronate, zolendronate, and pharmaceutically acceptable salts thereof. Also, tablets containing combinations of bisphosphonates are similarly prepared.

What is claimed is:

1. A pharmaceutical tablet, comprising:
   (a) from about 0.5 to 40% by weight of a bisphosphonic acid or a pharmaceutically acceptable salt or ester thereof; and
   (b) from about 60 to 99.5% by weight of excipients, said excipients comprising a diluent selected from the group consisting of anhydrous lactose or hydrous fast flow lactose, or mixtures thereof;
   a binder;
   a disintegrant; and
   a lubricant;
   which is coated with a discontinuous wax polish.

2. A pharmaceutical tablet according to claim 1 wherein said wax is selected from the group consisting of apple peel wax, avocado wax, bayberry wax, beeswax, candelilla wax, carnauba wax, ceresin, cetyl esters, hydrogenated jojoba oil, hydrogenated jojoba wax, hydrogenated microcyrstalline wax, hydrogenated rice bran wax, hydrolyzed beeswax, jojoba butter, jojoba esters, jojoba wax, lanolin wax, microcrystalline wax, mink wax, montan acid wax, montan wax, orange peel wax, ouricury wax, oxidized beeswax, oxidized micorcrystalline wax, ozokerite, palm kernel wax, paraffin wax, paraffin, PEG-6 beeswax, PEG-8 beeswax, Peg-12 beeswax, PEG-20 beeswax, PEG-12 carnauba, potassium oxidized microcrystalline wax, rice wax, shellac wax, spent grain wax, sulfurized jojoba oil, synthetic beeswax, synthetic candelilla wax, synthetic carcauba, synthetic japan wax, synthetic jojoba oil, synthetic wax, and mixtures thereof.

3. A pharmaceutical tablet according to claim 2 wherein said bisphosphonic acid is selected from the group consisting of
   4-amino-1-hydroxybutylidene-1,1-bisphosphonic acid;
   N-methyl-4-amino-1-hydroxybutylidene-1,1-bisphosphonic acid;
   4-(N,N-dimethylamino)-1-hydroxypropylidene-1,1-bisphosphonic acid;
   3-amino-1-hydroxypropylidene-1,1-bisphosphonic acid;
   3-(N,N-dimethylamino)-1-hydroxypropylidene-1,1-bisphosphonic acid;
   1-hydroxy-3-(N-methyl-N-pentylamino)propylidene-1,1-bisphosphonic acid;
   1-hydroxy-2-[3-pyridyl]ethylidene-1,1-bisphosphonic acid; and
   4-(hydroxymethylene-1,1-bisphosphonic acid) piperidene;
   or a pharmaceutically acceptable salt or ester thereof.

4. A pharmaceutical tablet according to claim 3 wherein said bisphosphonic acid is 4-amino-1-hydroxybutylidene-1,1-bisphosphonic acid or a pharmaceutically acceptable salt thereof.

5. A pharmaceutical tablet according to claim 4 wherein said bisphosphonic acid is 4-amino-1-hydroxybutylidene-1,1-bisphosphonic acid monosodium salt trihydrate.

6. A pharmaceutical tablet according to claim 5 wherein said diluent is anhydrous lactose, said binder is microcrystalline cellulose, said disintegrant is croscarmellose sodium, and said lubricant is magnesium stearate.

7. A pharmaceutical tablet according to claim 2 wherein said wax is carnauba wax.

8. A pharmaceutical tablet according to claim 7 comprising from about 5 mg to about 70 mg of 4-amino-1-hydroxybutylidene-1,1-bisphosphonic acid, measured on an alendronic acid active weight basis.

9. A process for the preparation of a pharmaceutical tablet comprising:
   (a) forming a mixture by mixing a bisphosphonic acid or a pharmaceutically acceptable salt or ester thereof, with a diluent, selected from the group consisting of anhydrous lactose or hydrous fast flow lactose, or mixtures thereof, a dry binder, a disintegrant, and optionally one or more additional ingredients selected from the groups consisting of:
   compression aids,
   flavors,
   flavor enhancers,
   sweeteners and
   preservatives;
   (b) lubricating the mixture with a lubricant;
   (c) compressing the resultant lubricated mixture into a desired tablet form; and
   (d) coating the desired tablet with a wax to form a discontinuous wax polish.

10. A process according to claim 9 wherein said wax is selected from the group consisting of apple peel wax, avocado wax, bayberry wax, beeswax, candelilla wax, carnauba wax, ceresin, cetyl esters, hydrogenated jojoba oil, hydrogenated jojoba wax, hydrogenated microcyrstalline wax, hydrogenated rice bran wax, hydrolyzed beeswax, jojoba butter, jojoba esters, jojoba wax, lanolin wax, microcrystalline wax, mink wax, montan acid wax, montan wax, orange peel wax, ouricury wax, oxidized beeswax, oxidized micorcrystalline wax, ozokerite, palm kernel wax, paraffin wax, paraffin, PEG-6 beeswax, PEG-8 beeswax, Peg-12 beeswax, PEG-20 beeswax, PEG-12 carnauba, potassium oxidized microcrystalline wax, rice wax, shellac wax, spent grain wax, sulfurized jojoba oil, synthetic beeswax, synthetic candelilla wax, synthetic carcauba, synthetic japan wax, synthetic jojoba oil, synthetic wax, and mixtures thereof.

11. A process according to claim 10 wherein said bisphosphonic acid is selected from the group consisting of
   4-amino-1-hydroxybutylidene-1,1-bisphosphonic acid;
   N-methyl-4-amino-1-hydroxybutylidene-1,1-bisphosphonic acid;
   4-(N,N-dimethylamino)-1-hydroxypropylidene-1,1-bisphosphonic acid;
   3-amino-1-hydroxypropylidene-1,1-bisphosphonic acid;
   3-(N,N-dimethylamino)-1-hydroxypropylidene-1,1-bisphosphonic acid;
   1-hydroxy-3-(N-methyl-N-pentylamino)propylidene-1,1-bisphosphonic acid;
   1-hydroxy-2-[3-pyridyl]ethylidene-1,1-bisphosphonic acid; and
   4-(hydroxymethylene-1,1-bisphosphonic acid) piperidene;
   or a pharmaceutically acceptable salt or ester thereof.

12. A process according to claim 11 wherein said bisphosphonic acid is 4-amino-1-hydroxybutylidene-1,1-bisphosphonic acid or a pharmaceutically acceptable salt thereof.

13. A process according to claim 12 wherein said bisphosphonic acid is 4-amino-1-hydroxybutylidene-1,1-bisphosphonic acid monosodium salt trihydrate.

14. A process according to claim 13 wherein said diluent is anhydrous lactose, said binder is microcrystalline cellulose, said disintegrant is croscarmellose sodium, and said lubricant is magnesium stearate.

15. A process according to claim 14 wherein no additional water is added to the mixture prior to compressing.

16. A process according to claim 15 wherein said process is carried out at ambient temperature.

17. The process according to claim 16 wherein the discontinuous wax polish is carnauba wax.

18. A pharmaceutical tablet, comprising a bisphosphonic acid or a pharmaceutically acceptable salt or ester thereof; and excipients, said excipients comprising a diluent, a binder, a disintegrant, and a lubricant;

wherein said tablet is coated with a discontinuous wax polish.

* * * * *